United States Patent [19]

Ferrari et al.

[11] 4,229,450
[45] * Oct. 21, 1980

[54] CARBAMATES OF HOMOLYSERGOLS (8β-HYDROHYETHYLERGOLINES) AND COMPOSITIONS THEREOF

[75] Inventors: Giorgio Ferrari; Vittorio Vecchietti, both of Milan, Italy

[73] Assignee: Simes Societa Italiana Medicinali e Sintetici S.p.A., Milan, Italy

[*] Notice: The portion of the term of this patent subsequent to Apr. 22, 1997, has been disclaimed.

[21] Appl. No.: 3,931

[22] Filed: Jan. 16, 1979

[30] Foreign Application Priority Data

Jan. 26, 1978 [GB] United Kingdom .................. 3262/78

[51] Int. Cl.³ .................... C07D 457/02; A61K 31/48
[52] U.S. Cl. ......................... 424/248.52; 424/248.55; 424/250; 424/261; 544/125; 544/361; 546/67; 260/244.4
[58] Field of Search .............. 546/67, 68; 260/244.4; 424/261, 248.55, 248.52, 250; 544/125, 361

[56] References Cited

U.S. PATENT DOCUMENTS

| | | | |
|---|---|---|---|
| 3,944,582 | 3/1976 | Ferrari et al. ........................... | 546/67 |
| 3,972,883 | 8/1976 | Arcari et al. ........................... | 546/68 |

FOREIGN PATENT DOCUMENTS

753635 7/1970 Belgium .
1230260 4/1971 United Kingdom .

*Primary Examiner*—Henry R. Jiles
*Assistant Examiner*—R. W. Ramsuer
*Attorney, Agent, or Firm*—Cushman, Darby & Cushman

[57] ABSTRACT

Novel ergoline derivatives are disclosed having the general formula (I)

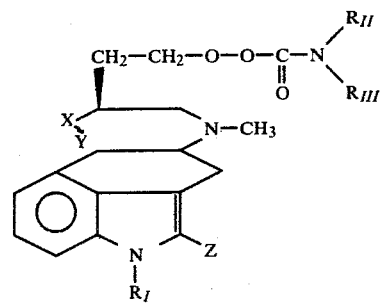

wherein $R_I$ is hydrogen, and alkyl radical ($C_1$ to $C_4$) either straight of branched chain, Z is hydrogen, bromine, S-$R_{IV}$ (in which $R_{IV}$ is an alkyl of from $C_1$ to $C_4$, $R_{II}$ is equal to $R_{III}$ and is an alkyl of from $C_1$ to $C_6$, or $R_{II}$ united with $R_{III}$ by-$(CH_2)_n$, with n from 0 to 7, to form simple heterocyclic compounds such as pyrrolidine, piperidine, hexamethyleneimine, or united with —$(CH_2)_n$—A—$(CH_2)_n$, with n equal to a number from 2 to 5 to form heterocyclic compounds such as A=0 and n=2 to give morpholine, A is N-$R_V$ and N=2 for piperazine, either substituted or unsubstituted, with $R_V$ being hydrogen, an alkyl of from $C_1$ to $C_4$, or a phenyl radical, the x—y bridge being a

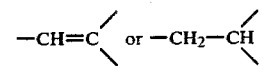

bond.

A method for the preparation of such compounds and pharmaceutical compositions thereof are also disclosed.

27 Claims, No Drawings

CARBAMATES OF HOMOLYSERGOLS (8β-HYDROHYETHYLERGOLINES) AND COMPOSITIONS THEREOF

This invention relates to the preparation of novel ergoline derivatives having the general formula (I) hereunder, and their use as novel medicaments:

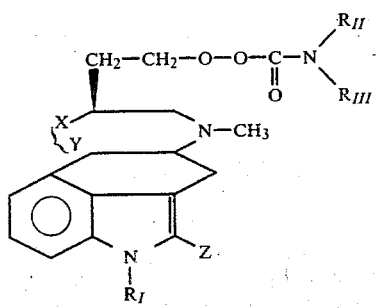

wherein $R_I$ is hydrogen, an alkyl radical ($C_1$ to $C_4$) either simple or branched, Z is hydrogen, bromine, S-$R_{IV}$ (in which $R_{IV}$ is an alkyl of from $C_1$ to $C_4$, $R_{II}$ is equal to $R_{III}$ and is an alkyl of from $C_1$ to $C_6$, or $R_{II}$ united with $R_{III}$ by -$(CH_2)_n$-, with n from 0 to 7, to form simple heterocyclic compounds such as pyrrolidine, piperidine, hexamethyleneimine, or united with -$(CH_2)_n$-A-$(CH_2)_n$, with equal to a number from 2 to 5 to form heterocyclic compounds such as A=O and n=2 to give morpholine, A is N-$R_V$ and N=2 for piperazine, either substituted or unsubstituted, with $R_V$ being hydrogen, an alkyl of from $C_1$ to $C_4$, or a phenyl radical, the x—y bridge being a CH=C or $CH_2$-C' bond.

The intermediates for the preparation of the novel compounds are the well known 8beta-hydroxyethylergolines, and are prepared with a novel procedure and with an improved yield from the corresponding ergolineacetic esters. The procedure involves the reduction of the ester with 4 molar equivalents of sodium bis-methoxy-ethoxy-aluminum hydride, followed by the decomposition of the excess of the reducing compound and the complex, elimination of the organic solvent, dilution with water and filtration to collect the pure 8beta-hydroxyethylergoline with yields of from 90% to 95%.

The subsequent reaction of the 8beta-hydroxyethylergoline with phenylcarbonate gives the compounds having the general formula (II) hereunder:

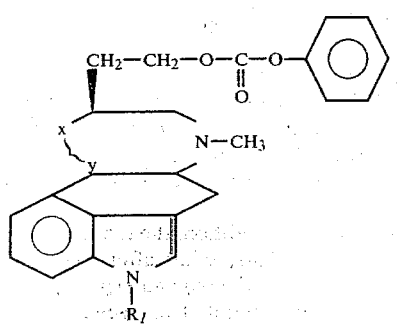

wherein $R_I$ and x—y have the meaning explained above.

The ensuing reaction of the carbonates having the general formula (II) with two molar equivalents of an amine having the general formula:

$$NH.R_{II}R_{III}$$

or, as an alternative, with one molar equivalent of an amine in the presence of one molar equivalent of $K_2CO_3$, triethylamine, di-isopropylmethylamine and other amines in an aprotic solvent such as dimethylformamide, dimethylsulfoxide, hexametapol and others, at temperatures comprised between 25° C. and 150° C. gives the compounds having the general formula (I) in which Z is a hydrogen.

The compounds having the general formula (I) in which Z=Br are prepared by reaction of the compounds having the general formula (I), in which Z=H, with a reactant selected from among N-bromosuccinimide, pyridinium bromide, perbromide, phenyltrimethylammonium bromide perbromide and others in solvents such as dioxane, tetrahydrofuran, hexametapol or mixtures thereof at a temperature comprised between $-10°$ C.+$100°$ C. More specifically, if the reaction is carried out within a mixture of tetrahydrofuran and hexametapol (9:1 vol.) with, for example, 1.6 molar equivalents of phenyltrimethylammonium perbromide at 20° C.-25° C. for 3 hours, after the usual processing the expected product is directly obtained with a high yield (80% to 90% of theory), that is to say the 2-brome derivative (Z=Br).

The compounds having the general formula (I) in which Z=S-$R_{IV}$ are conveniently obtained by reacting the compounds having the general formula (I) in which Z=H, with the appropriate chloride, $R_{IV}$-S-Cl. This reaction is carried out in aprotic solvents such as chloroform, methylene chloride, dichloroethane, trichloroethylene and others, at a low temperature (from 25° C. down to $-30°$ C.) with or without an acid acceptor such as $Na_2CO_3$, propylene oxide, triethylamine. The procedure for isolating and purifying the sulphur-containing compounds is greatly simplified if the raw reaction product is treated in alcoholic solvents such as ethanol with an excess of Ni-Raney at the reflux temperature of the solvent concerned. By so doing, the labile polysubstitution products, as well as the by-products of the reaction are decomposed or destroyed the purification of the products of the reactions according to the conventional procedure being thereby facilitated.

It has been found, moreover, that the compounds having the general formula (I) in which $R_1$ is an alkyl radical can be prepared starting from the compounds having the general formula (I) in which $R_1$ is hydrogen, by treating the latter products, in an aprotic solvent(s), initially with a base selected from among sodium hydride, sodamide, sodium methylate, potassium tert. butylate; and, thereafter, with the benzene sulphonates, the p.toluenesulphonates and methanesulphonates which have the general formula:

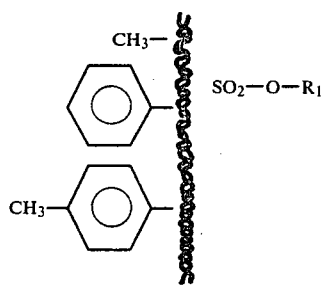

wherein $R_1$ has the meaning as defined above, but excluding H. It has been found that such a procedure is more convenient than the conventional one for this kind of substances ($KNH_2$ in liquid ammonia) due to the simplicity of the operations, the high yields and to the fact that no N-6 quaternization occurs.

The compounds of the present invention are generally crystalline solids and give pharmaceutically acceptable salts both with inorganic acids such as hydrochloric, hydrobromic, sulphuric, phosphoric acid and with organic acids such as methanesulphonic, malic, fumaric, tartaric, citric and lactic acid.

The novel compounds according to the present invention can be used as medicaments at dosage units comprised between 0.1 and 25 milligrams and their use comprise both the products as such and their pharmaceutically acceptable salts.

The pharmaceutical formulations comprise tablets, dragees, drops, ampoules and suppositories for oral, parenteral and rectal administration, respectively.

The solid formulations for oral use can be prepared by admixing the active ingredient with inerts and fillers such as lactose, starch, cellulose and its derivatives and, if desired, by compressing the mixture in the presence of lubricants such as stearates of magnesium and calcium, tablets or tablet cores being thus obtained. The tablet cores can be coated with sugar compounded with gum Arabic, talc, titanium dioxide, dyes and lacquers.

The solid formulations for oral use can also be compounded in the form of capsules of hard or soft gelatin. The latter contains the active principle in the form of a solution or a suspension in an appropriate liquid such as polyethylene glycol in the presence of stabilizers such as ascorbic acid or sodium metabisulphite. The solid formulation can also be so compounded as to ensure a delayed delivery (such as timecapsules).

The solutions for parenteral use or the drops for oral use can be prepared by dissolving the active ingredient in an appropriate solubilizing agent such as water, alcohol, glycerol or their mixtures so as to obtain solutions having concentrations of from 0.1% to 5%.

Lastly, for the rectal administration, the active principle can be diluted with appropriate suppository masses such as synthetic or natural triglycerides (such as cocoa butter) or can be compounded in gelatin capsules for rectal use.

It has been ascertained that the compounds having the formula (I) are endowed with interesting pharmcological properties when assayed on test animals with the methods and test procedures known to those skilled in the art. More particularly, it has been seen that a few of the compounds as described in the present specification display powerful anti-hypertensive, anti-asthmatic and anti-depressant activities. For these compounds a possible therapeutic use in the diseases of the circulatory system, the respiratory system and the central nervous system is predictable.

It has been found, in the test indicated by Goose and Blair, Immunology, 16, 749 (1969) for passive cutaneous anaphylaxis, PCA, that the compounds XIV, VII and XVII possess an outstanding activity which is shown in the following Table:

| $ED_{100}$ in milligrams per kilogram b/w | | | |
|---|---|---|---|
| XIV | 1 i.v. | Na chromoglycate | 5 i.v. |
|  | 5 os |  |  |
| VII | 1 i.v. |  | 5 i.v. |
|  | 5 os |  |  |
| XVII | 0.5 i.v. |  | 5 i.v. |
|  | 1 os |  |  |

As can be seen, such compounds possess an $ED_{100}$ which is at least 10 times smaller that that of sodium chromoglycate. In addition, such compounds are active by oral route at extremely low dosage levels (from 1 to 5 milligrams per kilogram b.w.) differently from the reference compound which proves to be inactive if administered by the oral route.

It has also been found that the compounds XV and V in naturally hypertension-prone rats behave like powerful anti-hypertensive agents having a long-lasting action.

As regards the corresponding test, see: Okamota K. et al. in "Spontaneous hypertension its pathogenesis and Complication—Okamota K. Ed. Springler Verlag—Berlin 1972, pag 1–8".

The $ED_{100}$ ranges from 5 to 25 milligrams per kilogram b.w. orally, which can be compared to that of reserpine and of hydralazine.

Lastly, it has been ascertained that the compounds XIII, VI, XVIII and XIX are powerful anti-depressants which are much more active of the imipramine which has been taken as the reference compound.

The table shows the results which have been obtained in a more conspicuous way.

Test for antagonism of the ptosis from reserpine (Askew, Life Sciences, 2, 725 (1963).

| $ED_{100}$ in milligrams per kilogram b.w. orally | | | |
|---|---|---|---|
| XIII | 0.1 | imipramine | 25 |
| VI | 0.005 |  | 25 |
| XVIII | 0.025 |  | 25 |
| XIX | 0.05 |  | 25 |

As can be seen, the activity can be observed yet at dosages which are 250, 1000 and 5000 times lower than those of the reference compound.

EXAMPLE 1

A solution of 14 grams of methyl homolysergate in 200 mls benzene in supplemented, with stirring and under a nitrogen blanket, with 55 mls, of sodium bismethoxy-ethoxy-aluminium hydride, the solution being 70% in benzene, so as to maintain gentle reflux conditions.

On completion of the addition, the reaction is allowed to proceed for two hours, whereafter the reaction is stopped with methanol (50 mls) and $H_2O$ (30 mls). The resultant mixture is evaporated in vacuum to dryness and the residue is taken up with 200 mls of a 5% NaOH solution. The insoluble solid is collected on a filter, washed thoroughly with water and dried, in a vacuum over $P_2O_5$.

By so doing, there are obtained 12 grams of homolysergol (D-6-methyl-9,10-didehydro-8beta-ergolene ethanol), m.p. 217°–219° C. having an $[\alpha] = +38.16°$ ($c = 0.63$ $C_5H_5N$) virtually unitary in t.l.c. In a similar manner, there is prepared the di-hydrohomolysergol (D-6-methyl-8beta-ergolene methanol) starting from the methyl dihydrohomolysergate.

EXAMPLE 2

A suspension of 8.5 grams of dihydro-homolysergol (D-6-methyl-8beta-ergolene ethanol) in 170 mls pyridine cooled to 5° C. is slowly supplemented by 6.4 grams of phenyl chlorocarbonate. Stirring at room temperature (22° C.) is continued during 15 hours whereafter the mixture is poured in ice water (500 mls). The precipitated solid is collected on a filter, washed with water and methanol and dried in vacuum over $P_2O_5$. There are obtained 12.3 grams of the phenylcarbonate of the dihydro-homolysergol (I) (D-6-methyl-8beta-(phenoxycarbonyloxyethyl) ergoline) with a virtually quantitative yields. The pure sample as obtained by crystallization from benzene has the following characteristic date: m.p. 172°–4° C. $[\alpha] - 62°$ ($c = 0.5$ $C_5H_5N$) UV $\lambda_{max}^{MeOH}$ $\mu m$ 282 ($\epsilon 31400$) m$\mu$ 226 ($\epsilon 31400$) m$\mu$ 292–294 flex paint. For $C_{24}H_{26}N_3O_2$ calcd: C% 73.82; H% 6.71; N% 7.17; found: C% 73.38; H% 6.31; N% 7.10.

In quite a similar way there is prepared ther phenylcarbonate of the homolysergol D-6-methyl-8beta-(phenoxycarbolynoxyethyl)-9,10-didehydro ergoline) (II): this is a solid which is easily decomposed and that it has not been possible to characterize.

EXAMPLE 3

A solution of 4 grams of D-6-methyl-8beta-(phenoxycarbonyloxyethyl)-9,10-dehydroergoline (raw) in 25 mls of dimethyl formamide, containing 8 grams of hexamethyleneimine is heated to 60° C.–70° C. during 15 hours and then poured in ice water. The precipitated product is collected on a filter, washed with water, dried and chromatographically analysed on 100 grams of $SiO_2$, deactivated with 5% of water, eluting with $CH_2Cl_2$ containing 1% of methanol. By so doing, there are obtained, upon crystallization, from ethyl acetate, 1.6 grams of D-6-methyl-8beta-(perhydroazepinylcarbonyloxyethyl)-9,10-didehydroergoline (III) having the following characteristic data: m.p. 191°–193° C. $[\alpha] + 27.6$ ($c = 0.5$ $C_5H_5N$) UV $\lambda_{max}^{MeOH}$ m$\mu$ 311 ($\epsilon 9650$) m$\mu$ 242 ($\epsilon 21000$) m$\mu$ 226 ($\epsilon 23600$). For $C_{24}H_{31}N_3O_2$ (M+393) calcd. % 73.25; H% 7.94; N% 10.68; found: C% 73.38; H% 7.78; N% 10.57.

In quite a similar way, there are prepared the compounds VII, VIII, IX, X, XI, XII, XIII.

EXAMPLE 4

To a solution of 10 grams of D-6-methyl-8beta-(morpholinocarbonyloxyethyl) ergoline in 150 mls of tetrahydrofuran containing 10% of hexamethylenephosphorotriamide there is added dropwise a solution of 15.7 grams of phenyltrimethylammonium bromide, perbromide in 50 mls of tetrahydrofuran. On completion of such an addition, the mixture is stirred at room temperature for 3 hours, whereafter the reaction is stopped by adding, in the order given, 2 grams of sodium bisulphite in 20 mls of $H_2O$, and 15 grams of $NaHCO_3$ in 150 mls of $H_2O$. The resultant mixture is then diluted with 500 mls of water and extracted with ether (3 extr. with 300 mls ether each). The resultant residue which has been obtained by evaporating off the ether is dissolved in $CH_2Cl_2 + 5\%$ methanol and filtered on a short column of $SiO_2$ which had been deactivated with the 10% of $H_2O$ (100 grams). By so doing, there are obtained 10.5 grams of D-2-bromo-6-methyl-8beta-(morpholinocarbonyloxyethyl) ergoline (IV) in a state of virtual purity. The product as crystallized from ethyl acetate exhibits the following specifications: m.p. 132°–134° C. $[\alpha] - 77$ ($c = 0.5$ $C_5H_5N$) UV $\lambda_{max}^{MeOH}$ m$\mu$ 280 ($\epsilon 8900$) m$\mu$ 227 ($\epsilon 31700$). For $C_{22}H_{28}BrN_3O_3$ (M+463-461-) Calcd. C% 57.14; H% 6.10; N% 9.09; found: C% 57.11; H% 5.74; N% 8.65.

The compound XIV is prepared very much in the same way.

EXAMPLE 5

A solution of 10 grams of 6-methyl-8beta-(morpholino-carbonyloxyethyl) ergoline in 300 mls of $CHCl_3$ is chilled to $-60°$ C. and treated with 3.3 grs of methylsulphinyl chloride. After a 30-minutes stirring at $-30°$ C. the mixture is diluted with 100 mls of a 5% solution of $NaHCO_3$ and the organic phase is separated. This latter phase is evaporated to dryness and the residue dissolved in 100 mls of 95% ethanol is refluxed during 3 hours with 100 grams of Ni-Raney. The nickel is filtered off and the ethanol is evaporated in vacuum. The residue, upon chromatography on $SiO_2$ deactivated with the 10% of $H_2O$ (eluant $CH_2Cl_2$ with 1% of methanol) gives 7.1 grams of a unitary product in the form of an amorphous solid which is converted into a crystalline maleate by treatment with a stoichiometrical amount of maleic acid in ether. Upon crystallization from 95% ethanol, there is obtained the D-2-methylthio-6-methyl-8beta-(morpholinocarbonyloxyethyl) ergoline maleate (V), pure, which has the following specifications: m.p. 215°–217° C. $[\alpha] - 41$ ($c = 0.5$ $C_5H_5N$) $\lambda_{max}^{MeOH}$ m$\mu$ 290 ($\epsilon 13700$) m$\mu$ 219 ($\epsilon 64000$). For $C_{27}H_{35}N_3O_7S$ (M+429) Calcd.: C% 59.43; H% 6.46; N% 7.70; Found: C% 59.96; H% 6.22; N% 7.77.

The compound XVI is prepared very much in the same way.

EXAMPLE 6

To a solution of D-2-bromo-6-methyl-8beta-(perhydroazepinylcarbonyloxyethyl) ergoline in 15 mls of dimethylformamide there are added, in increments, 383 milligrams of 80% sodium hydride. On completion of the addition, the reaction mixture is heated to 40° C. during 1 hour whereafter it is cooled to 18° C.–20° C. and 1.3 grams of methyl p.toluene sulphonate are slowly added thereto. After one hour of stirring at room temperature, the mixture is poured in water and the amorphous precipitate is collected on a filter and dried ove $P_2O_5$. The dried raw product is dissolved in acetone, decolorized with charcoal and treated with a stoichiometrical quantity of maleic acid. In this way there is obtained, with a yield of 90%, the maleate of the D-2-bromo-1,6-dimethyl-8beta-(perhydroazepinylcarbonyloxyethyl) ergoline (VI) which has the following specifications: m.p. 166°–168° C. (acetone) $[\alpha] - 44°$ ($c = 0.5$ $C_5H_5N$) UV $\lambda_{max}^{MeOH}$ m$\mu$ 286 ($\epsilon 9850$) m$\mu$ 226 ($\epsilon 40500$) m$\mu$ 210 ($\epsilon 37700$). For $C_{29}H_{38}BrN_3O_6$ (M+489-487) Calcd.: C% 57.61; H% 6.33; N% 6.95; found: C% 57.73; H% 5.94; N% 6.82.

The compounds XV, XVII, XVIII and XIX are similarly prepared.

VII D-6-methyl-8beta-(perhydroazepinylcarbonyloxyethyl) ergoline m.p. 206°-208° C. (ethyl acetate) [α]−74 (c=0.5 C$_5$H$_5$N) UV λ$_{max}^{MeOH}$ mμ 294 (ε5500) mμ 284 (ε7000) mμ 226 (ε29000). For C$_{24}$H$_{33}$N$_3$O$_2$ (M+395) calcd.: C% 72.88; H% 8.41; N% 10.62; found: C% 72.94; H% 8.11; N% 10.64.

VIII D-6-methyl-8beta-(piperidinocarbonyloxyethyl) 9.10-didehydro ergoline, maleate: m.p. 206°-208° C. (EtOH 99%) [α]+41 (c=0.5 C$_5$H$_5$N) UV λ$_{max}^{MeOH}$ mμ 312 (ε9450) mμ 235 flex point. For C$_{27}$H$_{33}$N$_3$O$_6$ (M+379). Calcd.: C% 65.44; H% 6.71; N% 8.48; Found: C% 65.06; H% 6.26; N% 8.39.

IX D-6-methyl-8beta-(piperidinocarbonyl oxyethyl) ergoline goline m.p. 196°-198° C. (MeOH) [α]-82.2 (c=0.5 C$_5$H$_5$N) UV λ$_{max}^{MeOH}$ mμ 282 (ε5700) mμ 226 (ε30500) mμ 292 flex point. For C$_{23}$H$_{31}$N$_3$O$_2$ (M+381). Calcd.: C% 72.41; H% 8.19; N% 11.01; Found: C% 72.55; H% 7.84; N% 11.13.

X D-6-methyl-8beta(dimethylaminocarbonyloxyethyl)-9,10-didehydro ergoline: m.p. 185° C.-187° C. (ethyl acetate) [α]+13.1 (c=0.5 C$_5$H$_5$N) UV λ$_{max}^{MeOH}$ mμ 312 (ε9200) mμ 242 (ε20400) mμ 228 (ε23000). For C$_{20}$H$_{25}$N$_3$O$_2$ (M+339); Calcd.: C% 70.77; H% 7.42; N% 12.38; Found: C% 69.94; H% 7.69; N% 12.07.

XI D-6-methyl-8beta(dimethylaminocarbonyloxyethyl)ergoline m.p. 187° C.-189° C. (ethyl acetate) [α]−95 (c=0.5 C$_5$H$_5$N) UV λ$_{max}^{MeOH}$ mμ 282 (ε7250) mμ 226 (ε20200) mμ 294 flex point. For C$_{20}$H$_{27}$N$_3$O$_2$ (M+341) Calcd.: C% 70.35; H% 7.97; N% 12.31; Found: C% 70.00; H% 7.57; N% 12.57.

XII D-6-methyl-8beta(morpholinocarbonyloxyethyl)-9,10-didehydro ergoline maleate. m.p. 208° C.-210° C. (EtOH 99%) [α]+36 (c=0.5 C$_5$H$_5$N) UV λ$_{max}^{MeOH}$ mμ 312 (ε8750) mμ 213 (ε32000). For C$_{26}$H$_{31}$N$_3$O$_7$ (M+381) Calcd.: C% 62.76; H% 6.28; N% 8.45. Found: C% 61.33; H% 5.92; N% 8.08.

XIII D-6-methyl-8beta(morpholinocarbonyloxethyl)ergoline m.p. 179° C.-181° C. (ethyl acetate) [α]−72° (c=0.5 C$_5$H$_5$N) UV λ$_{max}^{MeOH}$ mμ 294 (ε5900) mμ 282 (ε7100) mμ 226 (ε28600). For C$_{22}$H$_{29}$N$_3$O$_3$ (M+383). Calcd.: C% 68.90; H% 7.62; N% 10.96 Found: C% 67.85; H% 7.31; N% 10.67.

XIV D-2-bromo-6-methyl-8beta(perhydroazepinylcarbonyloxyethyl) m.p. 143° C.-145° C. (ethyl acetate) [α]$_D^{20}$−83 (c=0.5 C$_5$H$_5$N) UV λ$_{max}^{MeOH}$ mμ 282 (ε10300) mμ 228 (ε36200). For C$_{24}$H$_{32}$BrN$_3$O$_2$ (M+ 475-473) Calcd.: C% 60.76; H% 6.80; N% 8.86; Found: C% 60.57; H% 6.36; N% 8.75.

XV D-1,6-dimethyl-8beta(perhydroazepinylcarbonyloxyethyl) ergoline maleate: m.p. 154° C.-155° C. (EtOH 99%) [α]$_D^{20}$−35.8 (c=0.5 C$_5$H$_5$N) UV λ$_{max}^{MeOH}$ mμ 290 (ε6550); mμ 224 (ε36500). For C$_{29}$H$_{39}$N$_3$O$_6$ (M$^{30}$ 409) Calcd.: C% 66.26; H% 7.48; N% 7.99; Found: C% 66.41; H% 7.55; N% 7.81.

XVI D-2-methylthio-6-methyl-8beta(perhydroazepinylcarbonyloxyethyl) ergoline maleate; m.p. 213° C.-216° C. (EtOH 99%) [α]$_D^{20}$−47° (c=0.5 C$_5$H$_5$N) UV λ$_{max}^{MeOH}$ mμ 290 (ε13400) mμ 223 (ε36000). For C$_{29}$H$_{39}$N$_3$O$_6$S (M$^{30}$ 441) Calcd.: C% 62.45; H% 7.05; N% 7.53; Found: C% 62.72; H% 6.45; N% 7.57.

XVII D-1,6-dimethyl-8beta-morpholinocarbonyloxyethyl) ergoline maleate; m.p. 143° C.-145° C. (EtOH 99%) [α]−37 (c=0.5 C$_5$H$_5$N) UV λ$_{max}^{MeOH}$ mμ 290 (ε6300) mμ 226 (ε35800). For C$_{27}$H$_{35}$N$_3$O$_7$ (M$^{30}$ 397) Calcd.: C% 63.14; H% 6.87; N% 8.18; Found: C% 62.84; H% 6.64; N% 7.99.

XVIII D-2-bromo-1,6-dimethyl-8beta(morpholinocarbonyloxyethyl) ergoline maleate. m.p. 170° C.-172° C. (EtOH 99%) [α]$_D^{20}$−38.1° (c=0.5 C$_5$H$_5$N) UV λ$_{max}^{MeOH}$ mμ 284 (ε10050) mμ 225 (ε41000). For C$_{27}$H$_{34}$BrN$_3$O$_7$ (M+ 477-475) Calcd.: C% 54.73; H% 5.98; N% 7.09; Found: C% 53.91; H% 5.49; N% 6.95.

XIX D-2-methylthio-1,6-dimethyl-8beta(morpholinocarbonyloxyethyl) ergoline maleate. m.p. 167° C.-169° C. (EtOH 99%) [α]$_D^{20}$−45 (c=0.5 C$_5$H$_5$N) UV λ$_{max}^{MeOH}$ mμ 288 (ε12250) mμ 224 (ε37000) mμ 210 (ε38300). For C$_{28}$H$_{37}$N$_3$O$_7$S (M+ 443) Calcd.: C% 60.09; H% 6.66; ;l N% 7.51; Found: C% 59.43; H% 5.91; N% 7.26.

We claim:

1. Novel ergoline derivatives having the general formula (I)

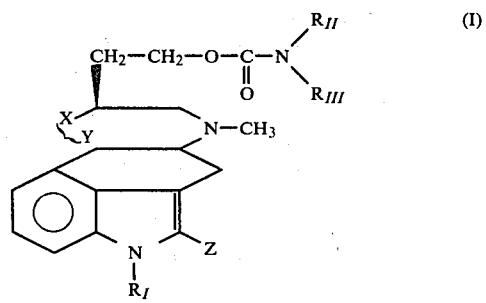

wherein R$_1$ is hydrogen, an alkyl radical (C$_1$ to C$_4$) either straight or branched chain.

Z is hydrogen, bromine, S-R$_{IV}$ (in which R$_{IV}$ is an alkyl of from C$_1$ to C$_4$, R$_{II}$ is equal to R$_{III}$ and is an alkyl of from C$_1$ to C$_6$, or R$_{II}$ united with R$_{III}$ form pyrrolidine, piperidine, hexamethyleneimine, morpholine or piperazine unsubstituted or N-substituted by C$_1$ to C$_4$ alkyl or phenyl, the x—y bridge being a

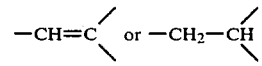

bond.

2. D-6-methyl-8beta(perhydroazepinylcarbonyloxyethyl)-9,10-didehydroergoline.

3. D-6-methyl-8beta(perhydroazepinylcarbonyloxyethyl)ergoline.

4. D-6-methyl-8beta(piperidinocarbonyloxyethyl)9.10-didehydro ergoline.

5. D-6-methyl-8beta-(piperidinocarbonyloxyethyl)ergoline.

6. D-6-methyl-8beta(dimethylaminocarbonyloxyethyl)-9,10-didehydro ergoline.

7. D-6-methyl-8beta(dimethylaminocarbonyloxyethyl)ergoline.

8. D-6-methyl-8beta(morpholinocarbonyloxyethyl)-9,10-didehydro ergoline.

9. D-6-methyl-8beta(morpholinocarbonyloxyethyl) ergoline.

10. D-2-bromo-6-methyl-8beta(morpholinocarbonyloxyethyl) ergoline.

11. D-2-bromo-6-methyl-8beta(perhydroazepinylcarbonyloxyethyl) ergoline.

12. D-2-methylthio-6-methyl-8beta(morpholine carbonyloxyethyl) ergoline.

13. D-2-methylthio-6-methyl-8beta(perhydroazepinylcarbonyloxyethyl) ergoline.

14. D-2-bromo-1,6-dimethyl-8beta(perhydroazepinylcarbonyloxyethyl) ergoline.

15. D-1,6-dimethyl-8beta(perhydroazepinylcarbonyloxyethyl) ergoline.

16. D-1,6-dimethyl-8beta(morpholinocarbonyloxyethyl) ergoline.

17. D-2-bromo-1,6-dimethyl-8beta(morpholinocarbonyloxyethyl) ergoline.

18. D-2-methylthio-1,6-dimethyl-8beta(morpholinocarbonyloxyethyl) ergoline.

19. A compound according to claim 1 where Z is bromine and $R_{II}$ and $R_{III}$ are united to form pyrrolidine, piperidine or hexamethyleneimine ring.

20. A pharmaceutical composition having antihypertensive activity, antiasthmatic activity or anti-depressant activity, characterized in that it contains a pharmaceutical carrier and as active principle in an amount effective for said activity a compound according to claim 1, or a parmaceutically acceptable salt thereof.

21. A pharmaceutical composition according to claim 20, of high antiasthmatic activity characterized in that it contains as active principle one of the compounds D-6-methyl-8beta(perhydroazepinylcarbonyloxyethyl)ergoline, D-2-bromo-6-methyl-8beta(perhydroazepinylcarbonyloxyethyl)ergoline, and D-1,6-dimethyl-8beta(-morpholinocarbonyloxyethyl)ergoline, such active principle possessing an $ED_{100}$ i.v. comprised between 0.5 and 1 mg/kg (sodium chromoglycate test) and an $ED_{100}$ per os comprised between 1 and 5 mg/kg.

22. A pharmaceutical composition according to claim 20, of high antihypertensive activity, characterized in that it contains as active principle one of the compounds D-2-methylthio-6-methyl-8beta(morpholinecarbonyloxyethyl)ergoline and D-1,6-dimethyl-8beta(perhydroazepinylcarbonyloxyethyl)ergoline, such active principle possessing an $ED_{100}$ comprised between 5 and 25 mg/kg per os.

23. A pharmaceutical composition according to claim 20, of high anti-depressant activity, characterized in that it contains as active principle one of the compounds D-6-methyl-8beta(morpholinocarbonyloxyethyl)ergoline, D-2-bromo-1,6-dimethyl-8beta(perhydroazepinylcarbonyloxyethyl)ergoline, D-2-bromo-1,6-dimethyl-8beta(morpholinocarbonyloxyethyl)ergoline and D-2-methyl-1,6-dimethyl-8beta(morpholinocarbonyloxyethyl)ergoline, such active principle possessing an $ED_{100}=0.1$; 0.005; 0.025; 0.05 mg/kg per os, respectively.

24. A pharmaceutical composition according to claim 20, characterized in that it contains such active principle in a dose selected between 0.1 and 25 mg.

25. A pharmaceutical composition according to claim 20, characterized in that it is in a sustained release form.

26. A pharmaceutical composition according to claim 23 wherein the compound is D-2-bromo-1,6-dimethyl-8beta(perhydroazepinylcarbonyloxyethyl)ergoline.

27. A pharmaceutical composition according to claim 20 where Z is bromine and $R_{II}$ and $R_{III}$ are united to form a pyrrolidine, piperidine or hexamethyleneimine ring.

* * * * *